(12) United States Patent
Burton et al.

(10) Patent No.: US 7,753,903 B1
(45) Date of Patent: Jul. 13, 2010

(54) METHOD AND IMPLANTABLE APPARATUS FOR THE INTRA-OSSEAL MONITORING OF BIOLOGICAL SUBSTANCES IN THE BONE MARROW, INCLUDING WITHOUT LIMITATION, GLUCOSE, THE INTRA-OSSEAL DELIVERY OF DRUGS, INCLUDING WITHOUT LIMITATION, INSULIN, THE INTEGRATION OF FOREGOING, AND RELATED OR ANCILLARY MATTERS

(75) Inventors: Charles Victor Burton, St. Paul, MN (US); Robert Harold Lovett, Savage, MN (US)

(73) Assignee: Pauneeforte Technologies, LLC, Shakopee, MN (US)

( * ) Notice: Subject to any disclaimer, the term of this patent is extended or adjusted under 35 U.S.C. 154(b) by 105 days.

(21) Appl. No.: 11/656,341

(22) Filed: Jan. 22, 2007

Related U.S. Application Data

(60) Provisional application No. 60/764,854, filed on Feb. 2, 2006.

(51) Int. Cl.
 *A61K 9/22* (2006.01)
(52) U.S. Cl. .................... 604/891.1; 600/316; 600/365; 604/66
(58) Field of Classification Search ................. 600/316, 600/322, 341, 347, 365
 See application file for complete search history.

(56) References Cited

U.S. PATENT DOCUMENTS

| 5,305,745 | A | * | 4/1994 | Zacouto | ................... | 600/324 |
| 5,357,974 | A | * | 10/1994 | Baldridge | ................... | 600/567 |
| 2004/0193025 | A1 | * | 9/2004 | Steil et al. | ................... | 600/316 |

* cited by examiner

*Primary Examiner*—Eric F Winakur
*Assistant Examiner*—Etsub D Berhanu
(74) *Attorney, Agent, or Firm*—Z. Peter Sawicki; Westman, Champlin & Kelly, P.A.

(57) ABSTRACT

A method for monitoring biological substances found in the bloodstream include implanting in-vivo a pedestal such that a sensor mounted on the pedestal extends into the bone marrow for sensing the biological substance. A transmitter is included for transmitting signals from the sensor to a receiver.

7 Claims, 5 Drawing Sheets

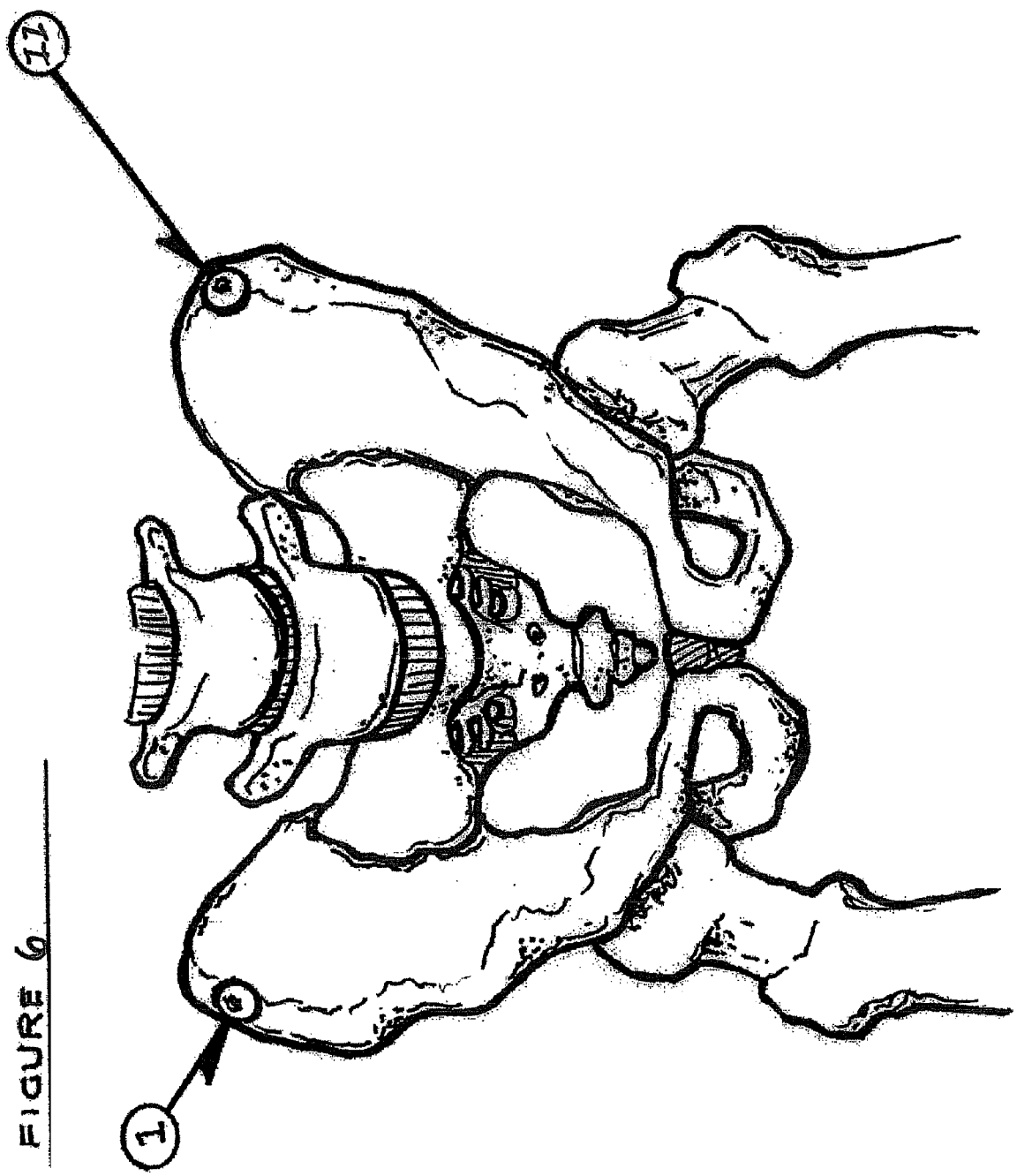

US 7,753,903 B1

METHOD AND IMPLANTABLE APPARATUS FOR THE INTRA-OSSEAL MONITORING OF BIOLOGICAL SUBSTANCES IN THE BONE MARROW, INCLUDING WITHOUT LIMITATION, GLUCOSE, THE INTRA-OSSEAL DELIVERY OF DRUGS, INCLUDING WITHOUT LIMITATION, INSULIN, THE INTEGRATION OF FOREGOING, AND RELATED OR ANCILLARY MATTERS

CROSS REFERENCE TO RELATED APPLICATION(S)

The present application claims priority from Provisional Application No. 60/764,854, filed on Feb. 2, 2006, which is hereby incorporated by reference in its entirety.

FIELD OF THE INVENTION

The present invention relates to an implantable device for the testing for, and the delivery of substances into, the intra-osseal space within a mammal, particularly in a human being, to monitor biological substances in the intra-osseal space which is similar to the blood stream, particularly for the determination of glucose content, the deliver of drugs, particularly insulin into the intra-osseal bone marrow, and the integration of the foregoing, as well as related and ancillary matters and the methods respecting the foregoing.

BACKGROUND OF THE INVENTION

Currently, there are a large number of methods and devices designed to detect blood glucose levels and particularly hypoglycemia in human beings with diabetes mellitus. The traditional method for monitoring glucose levels is by "finger sticking" and measuring the glucose level from the blood expressed. Avoiding the pain and discomfort of "finger sticking" has promoted the development of the non-invasive techniques such as measuring glucose concentration using the absorption of light in the infrared spectrum. Another approach has been subcutaneous fluid testing using either a disposable subcutaneous glucose monitor or the relatively permanent implantation of glucose sensors. Additionally, a noninvasive method has been developed in which impedance spectroscopy or similar methods are used to measure glucose concentrations. These various methods and devices have suffered in the reliability of the test results. The most accurate present means of repeatedly and accurately monitoring blood substances is by an indwelling intravascular catheter. The problem with these is that their useful time is limited by tissue breakdown and infection.

SUMMARY OF THE INVENTION

The present invention relates to the development of a stable and reliable implanted device designed to utilize the intra-osseal bone marrow for the testing for, and delivery of substances into this body compartment within a mammal, particularly in a human being, to monitor biological substances in the blood stream, particularly the level of glucose, and the delivery of drugs, particularly insulin into this compartment as well as the integration of the foregoing, and related and ancillary matters and the methods respecting the foregoing.

BRIEF DESCRIPTION OF THE DRAWINGS

FIG. 6 is a schematic representation of the pelvic bone region of a human body indicating insertion points for the implanted drug monitoring device and the implanted drug delivery device.

DETAILED DESCRIPTION

The following statements A1, B1, and C1 summarize certain aspects of the invention described in this specification. They are no the claims in the sense of 35 U.S.C. §112:

Statement A1 It is an object of the invention to utilize the relationship between the bone marrow 10 and the intravascular system with respect to levels of similar substances in the blood stream by implanting a pedestal 3 into bone 9, particularly the ilium but alternatively in other areas with sufficient mass of intra-osseal bone marrow material and convenient to the external interrogation of the same by a patent.

Statement B1 It is an object of the invention to utilize the reliable relationship between bone marrow 9 and the intravascular system to provide drug delivery into the intra-osseal bone marrow compartment by implanting a pedestal into the surrounding bone, particularly the ilium but alternatively in other areas with sufficient mass of bone marrow material and in a manner as to not inhibit the contemporaneous monitoring of levels of substances, particularly glucose, in the blood stream.

Statement C1 It is an additional object of this invention to integrate the monitoring apparatus and the drug delivery apparatus with a wired or wireless connection.

Figure 1:
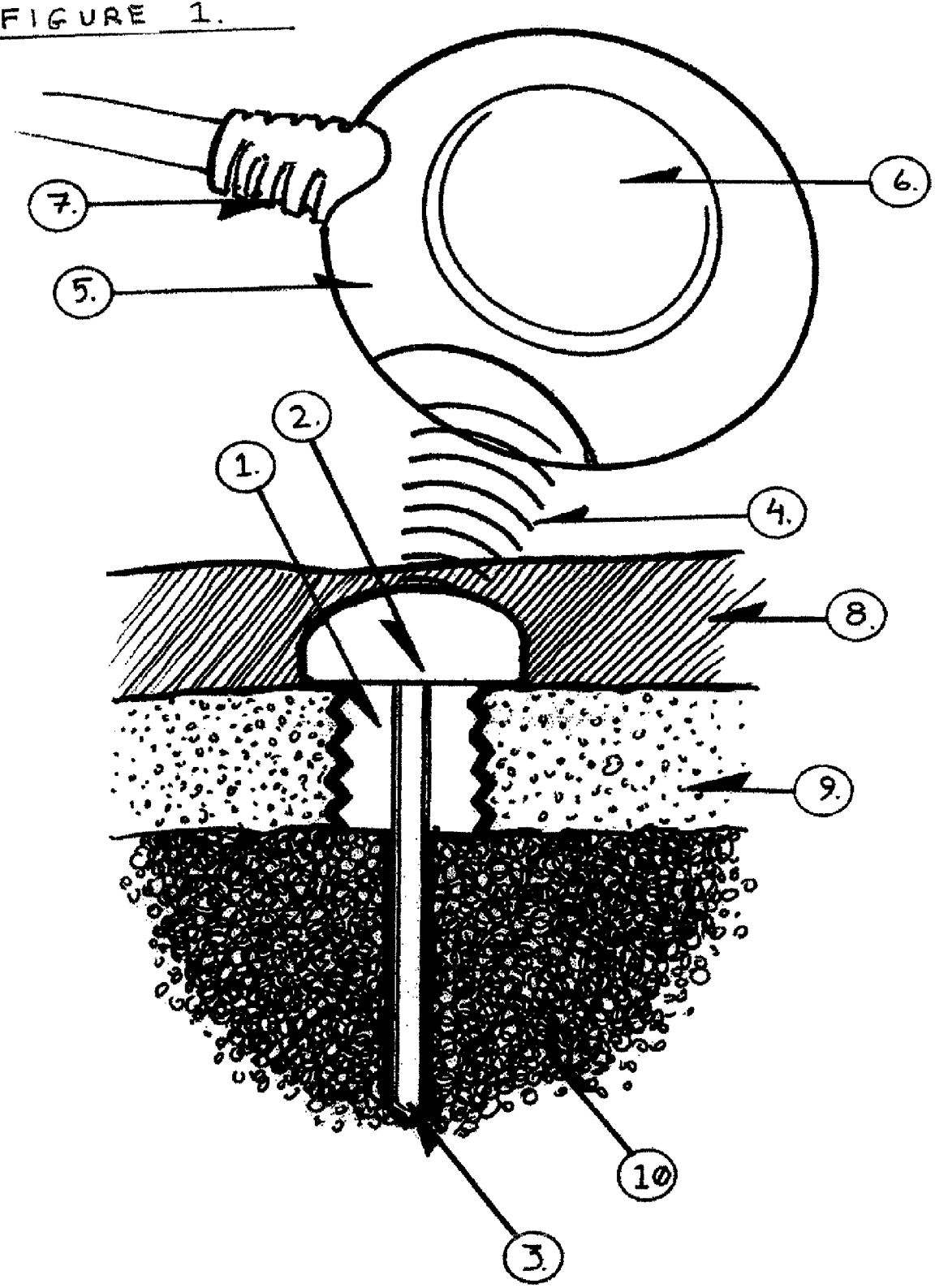
FIG. 1 is a schematic representation of the implanted monitoring device.

FIG. 1 is schematic representation of the implanted monitoring device 1. In one application the dermis 8 is populated with conductive material and electrical contact is direct. In another application the electrical contact is indirect (i.e., by radio frequency 4). A sensor 2 acts as a transmitter and receiver. It is either powered with a battery encased in a substance such as titanium or is powered externally be electrical emanations from the external interrogation device 5, which is also the transmitter and receiver 6 of the data generated by the implanted monitoring device 1. The internally placed sensor 2 includes a sensor at the end of the pedestal 3 that is implanted in the osseous exterior of the ilium 9 or a site of similar mass with access to a robust supply of blood marrow 10. The sensor 2 has a geodesic shape to permit interrogation from various angles. The monitor 3 may be electronic, chemical, or photometric. The interrogation phase may be by transmission of radio frequency, infra red light, or other forms of energy transmission 4. A communication link 15 is attached to the interrogation device to the sensor 16.

Figure 2:
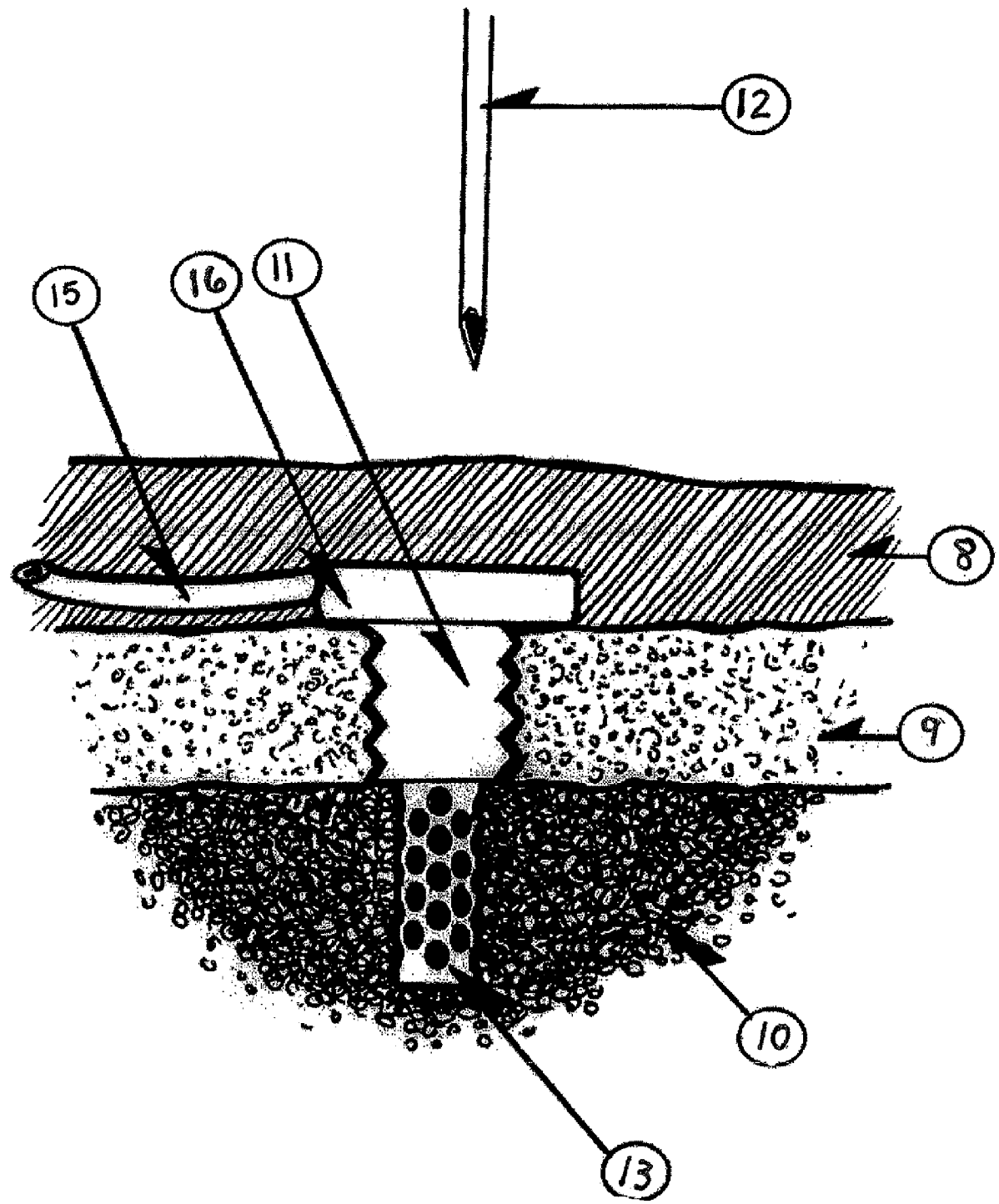
FIG. 2 is a schematic representation of the implanted drug delivery device.

FIG. 2 is schematic representation of the implanted drug delivery device 11. While the drug delivery device 11 is envisioned to be placed into the ilium 9 or similar osseous site of similar mass and access to a robust supply of blood marrow 10, the drug supply pod could be located remotely. The delivery of the drug could be occasioned by signals sent from the same external device 5 that interrogates the monitor 2.

Figure 3:
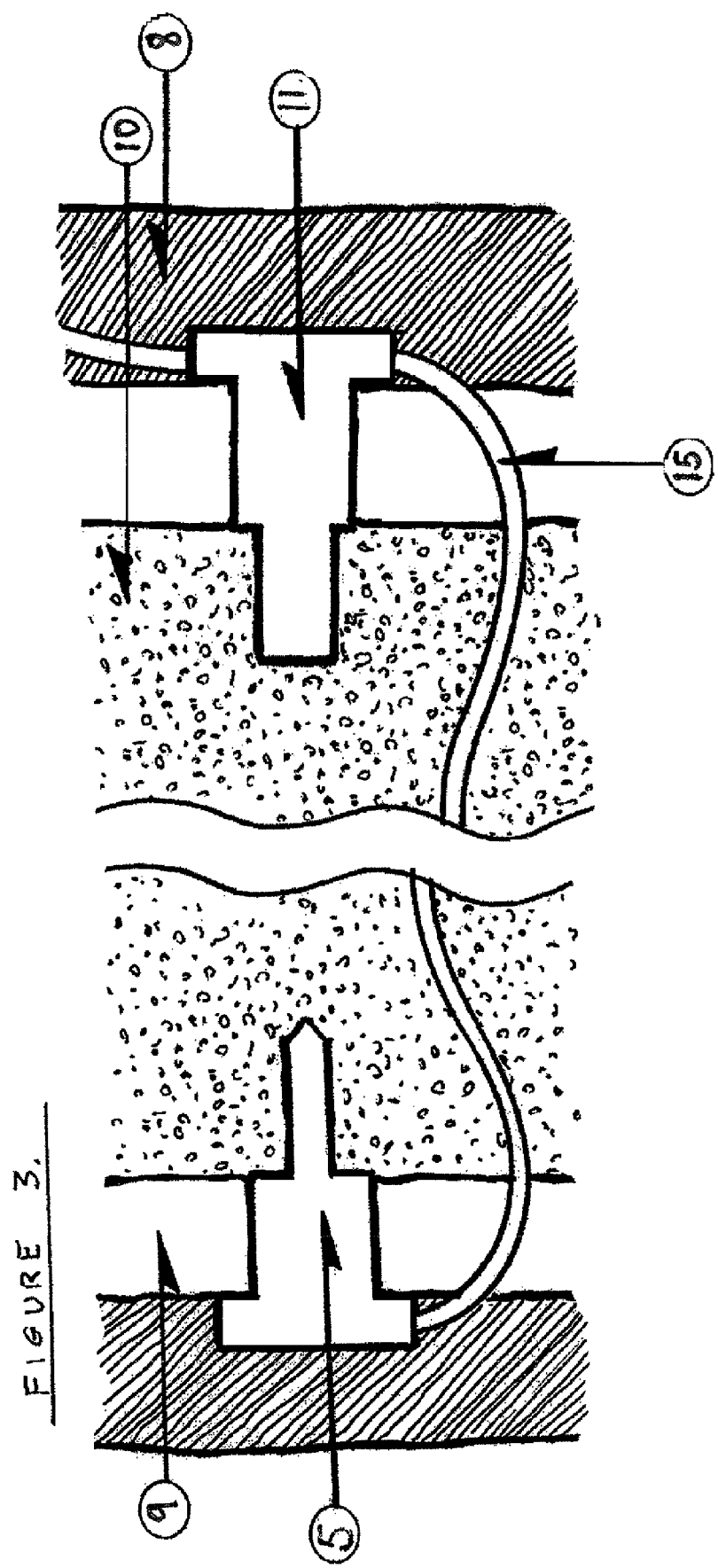
FIG. 3 is a schematic view of the implanted drug delivery device and the drug monitoring device implanted within the body.

FIG. 3 is the preferred embodiment of the integration of the implanted monitoring device 1 and the implanted drug delivery device 11. Here the implanted monitoring device 1 and the implanted drug delivery device 11 are placed on each ilium 5 and communicating through a wired 15 or unwired connection.

Figure 4:
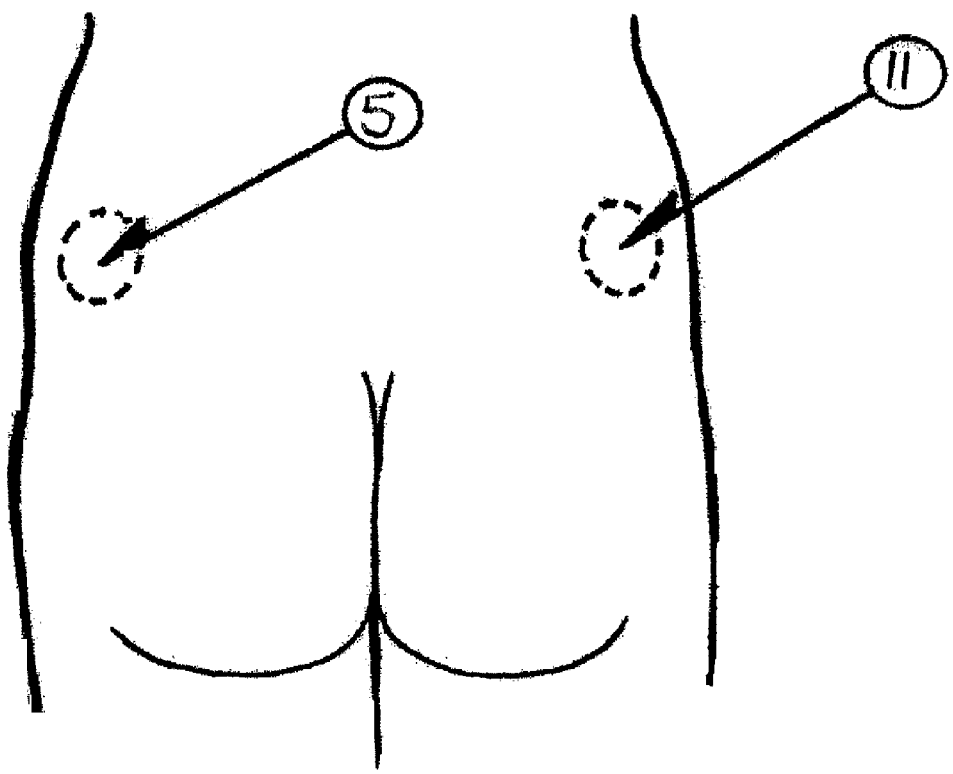
FIG. 4 is a view of the human body illustrating insertion points for the drug delivery device and the monitoring device.

FIG. 4 indicates the preferred location of implantation on the crest of the ilium 5. Alternative locations may be appropriate. Additionally, the implanted monitor and drug delivery device 11 could be integrated into a single apparatus or could remain separate but share a proximate location, provided the data generated by the monitor 1 does not become corrupted by the inflow of the substance, such as insulin, delivered by the drug delivery device 11.

Figure 5:
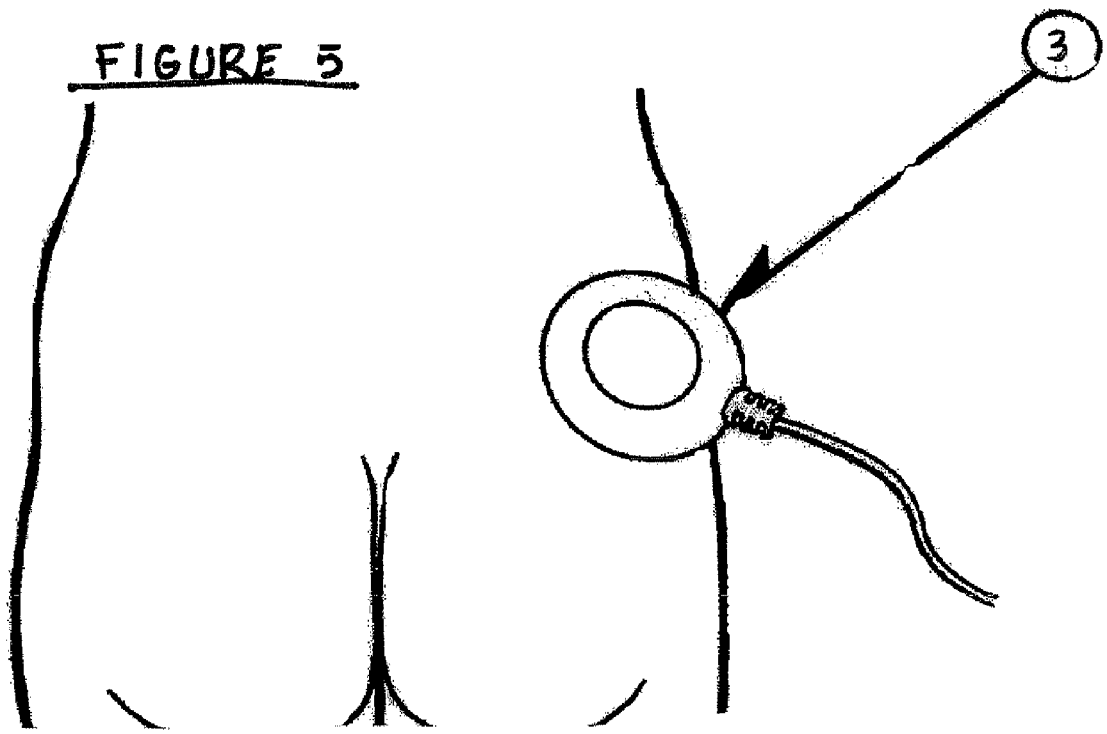
FIG. 5 is a view of the sensor placed over the implanted monitoring device.

FIG. 5 indicates the position of the transmitting sensor and coil 5 placed over the implanted pedestal 3 or 13.

Although the present invention has been described with reference to preferred embodiments, workers skilled in the art will recognize that changes may be made in form and detail without departing from the spirit and scope of the invention.

What is claimed is:

1. A method for monitoring and controlling glucose concentrations in a bloodstream comprising:
   implanting in-vivo a pedestal such that a sensor mounted on the pedestal extends into bone marrow for sensing the glucose concentration;
   sensing the concentration of glucose in the bloodstream with the sensor;
   implanting in-vivo a drug delivery device into the bone marrow;
   transmitting signals from the sensor to a receiver relating to the glucose concentration in the bloodstream; and
   transmitting signals from the receiver to the drug delivery device such that a dose of insulin is administered to the bone marrow of the patient to control the glucose concentration in the bloodstream.

2. The method of claim 1 and wherein the pedestal with the sensor and the drug delivery device are integrated into a single device.

3. The method of claim 1 and wherein the pedestal with the sensor and the drug delivery device are spaced apart from each other.

4. The method of claim 3 and wherein the pedestal with the sensor and the drug delivery device are implanted within an ilium.

5. The method of claim 4 and wherein the sensor and the drug delivery device are implanted within a crest of the ilium.

6. The method of claim 1 and wherein the signals transmitted from the sensor to the receiver are transmitted over an unwired connection.

7. The method of claim 1 and wherein the dose of insulin is administered to the bone marrow of the patient through a perforated pedestal positioned within the bone marrow.

* * * * *